United States Patent [19]

Narazaki

[11] 4,310,520

[45] Jan. 12, 1982

[54] SOLIDIFIED EMULSIFIABLE CONCENTRATE AND METHOD FOR APPLICATION THEREOF

[75] Inventor: Mitsutoshi Narazaki, Amagi, Japan

[73] Assignees: Mikasa Chemical Industry Company, Limited, Fukuoka; Mitsubishi Chemical Industries Limited, Chiyoda, both of Japan

[21] Appl. No.: 62,106

[22] Filed: Jul. 30, 1979

Related U.S. Application Data

[63] Continuation-in-part of Ser. No. 927,337, Jul. 24, 1978, abandoned.

[30] Foreign Application Priority Data

Jul. 30, 1977 [JP] Japan ................................. 52-91920
Oct. 28, 1977 [KR] Rep. of Korea ................. 2492/1977

[51] Int. Cl.$^3$ ..................... A01N 25/00; A01N 31/08; A01N 47/10; A01N 57/00
[52] U.S. Cl. ........................................ 424/200; 71/88; 71/93; 71/108; 71/DIG. 1; 424/213; 424/216; 424/218; 424/219; 424/222; 424/224; 424/225; 424/274; 424/300; 424/305; 424/306; 424/346; 424/353; 424/362

[58] Field of Search ............... 424/200, 213, 225, 219, 424/274, 362, 222, 224, 353, 306, 305, 300, 346, 216, 228

[56] References Cited

U.S. PATENT DOCUMENTS

| | | | |
|---|---|---|---|
| 3,459,836 | 8/1969 | Richter | 260/961 |
| 3,492,405 | 11/1970 | Hamm | 424/224 |
| 3,641,223 | 2/1972 | Schlor et al. | 424/222 |
| 3,764,698 | 10/1973 | Partos | 424/213 |

FOREIGN PATENT DOCUMENTS 38-6499 5/1963 Japan.
46-42800 12/1971 Japan.

*Primary Examiner*—Allen J. Robinson
*Attorney, Agent, or Firm*—Oblon, Fisher, Spivak, McClelland & Maier

[57] ABSTRACT

This invention relates to the production of a solidified emulsifiable concentrate for agricultural uses or sanitary uses by adsorbing a liquid substance containing an active ingredient sparingly soluble or totally insoluble in water and emulsifier into powdered cellulose. Said solidified emulsifiable concentrate becomes easily a stable emulsion suitable for practical use in contact with water.

18 Claims, 1 Drawing Figure

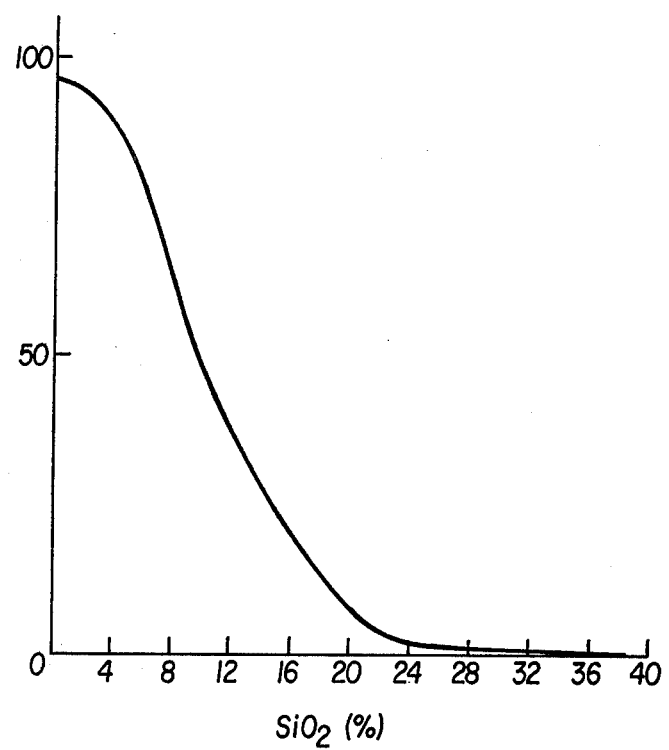

SOLIDIFIED EMULSIFIABLE CONCENTRATE AND METHOD FOR APPLICATION THEREOF

CROSS REFERENCE TO RELATED APPLICATIONS

The present application is a continuation-in-part of copending application Ser. No. 927,337 filed on July 24, 1978, now abandoned.

BACKGROUND OF THE INVENTION

1. Field of the Invention

This invention relates to a solidified emulsifiable concentrate and a method for the application thereof. By the term "solidified emulsifiable concentrate" used herein is meant a solid chemical preparation which has an emulsifiable concentrate supported on a carrier and which, upon mixture with water, forms a stable emulsion. And the term "agricultural uses" used in the specification hereof is not meant in a narrow sense of only embracing "uses with agricultural and horticultural produces:" but in a broad sense of embracing "uses with arboreal and forestal produces" in addition to those mentioned above.

2. The Prior Art

Chemicals for agricultural uses and for sanitary uses are generally sold and applied in the form of mixtures of active ingredients with various adjuvants selected to suit the particular purposes for which they are used. Generally, these chemicals are divided by their forms into dusts, granules, wettable powders, emulsifiable concentrates, solutions, etc. As a rule, wettable powders, emulsifiable concentrates and solutions are diluted with water immediately before application and are prepared respectively in the form of suspensions, emulsions and dilute solutions so as to suit their application by spraying. They are applied in the form of mist by means of a sprayer. Since they invariably use water as a carrier, their application calls for more human labor or motive force and proves more troublesome than the application of such solid fine-dust granules as dusts and granules. The droplets of liquid preparations so applied by spraying, however, have a particle diameter (generally from 0.2 to 0.1 mm) large enough to preclude otherwise possible drifting of droplets outside the areas of application. Thus, the application by spraying has an advantage that the possibility of active ingredients polluting the environment bordering on the areas of application is diminished and the consumption of chemicals is reduced. Of these chemicals which use water as a carrier, solutions and emulsifiable concentrates prove to be more desirable forms than wettable powders since, after their effects have been manifested, they are decomposed more quickly into non-toxic components by physical energies such as light and heat or by microorganisms. Where water is used as a carrier, those active ingredients which are sparingly soluble or totally insoluble in water cannot be prepared in the form of solutions and, therefore, must be used in the form of wettable powders or emulsifiable concentrates.

Wettable powders are preparations which have active ingredients supported on solid carriers and, therefore, can be handled as solid substances until they are diluted with water immediately before their actual application. In contrast, emulsifiable concentrates are liquid preparations which are obtained by dissolving active ingredients, as required, with organic solvents and adding suitable surface active agents to the resultant solutions and, therefore, are handled as liquid substances. Generally, liquid substances entail various inevitable disadvantages in terms of package and container, ease of handling, etc. as compared with solid substances. If emulsifiable concentrates could be converted into solid substances, the solidified emulsifiable concentrates so obtained would prove to be highly advantageous.

Attempts have so far been made for the development of methods capable of solidifying emulsifiable concentrates. For example, it is known to solidify an emulsifiable concentrate by causing the concentrate to be adsorbed on a granular carrier such as diatomaceous earth (Japanese patent publication No. 6499/1963). The product which is obtained by this method, however, is intended to be incorporated directly in its granular form into soil. It is also known to effect the solidification by using a fine-dust type or short-fiber type cellulose as a carrier (Japanese patent publication No. 42800/1971). This invention relates to granular agricultural chemicals for use in paddy fields and aims to permit solidified agricultural chemicals to be retained long in their suspended state under water and thereby enable their active ingredients to be released efficiently into inundating water. For this purpose, the solidified agricultural pesticides are specified to possess particle diameters in the range of from 4 to 35 mesh (by Tyler scale). As described above, these solidified preparations obtained by the known methods are intended for direct application in their granular forms. It has not yet been known to the art to produce solidified emulsifiable concentrations of the type which are diluted with water and applied in the form of stable emulsions.

Therefore, a general object of the present invention is to provide a solidified chemical preparation which, upon dilution with water, forms a stable emulsion.

Another object of the present invention is to provide a method for the application of a solidified chemical preparation obtained by causing an emulsifiable concentrate containing an active ingredient sparingly soluble or totally insoluble in water to be occluded in powdered cellulose, which method comprises mixing the solidified chemical preparation with water to form a stable emulsion and applying the emulsion to whatever is desired to be treated therewith.

SUMMARY OF THE INVENTION

The inventors made a study in search of a method capable of producing a solidified emulsifiable concentrate which, upon dilution with water, would give rise to a stable emulsion. They have, consequently, ascertained that a preparation obtained by having an emulsifiable concentrate occluded in powdered cellulose meets the purpose. The present invention has been accomplished on the basis of this knowledge.

Fundamentally, the solidified chemical preparations involved in the present invention are produced by mixing active ingredients with emulsifiers mixtures of particular compositions and, when necessary, additionally with organic solvents to form solutions and subsequently causing the solutions to be occluded in powdered cellulose.

BRIEF EXPLANATION OF THE DRAWING

The drawing is a graph showing the relation between the ratio of the quantities of powdered cellulose and white carbon used in accordance with the method of this invention and the ratio of emulsification. In the graph, the vertical axis is graduated for the ratio of emulsification and the horizontal axis for the quantity of $SiO_2$ used (% by weight based on total weight).

DETAILED DESCRIPTION OF THE INVENTION

The powdered cellulose which is used in the present invention is formed preponderantly of α-cellulose derived from vegetable origins as well known. Various preparations of powdered cellulose are marketed for use as extenders, mixing agents, carriers, etc. They come in various forms such as fibrous forms and crystalline forms and they also come in varying particle sizes and color tones. Users are to select them to suit the particular purposes for which they are used. For the purpose of this invention, the powdered cellulose tolerates presence therein of an inconspicuous amount of extraneous substances such as, for example, ashes, lignin and resins which originate in the raw material. Generally it is desirable that the water content should not exceed about 7% (by weight) and the resin content about 2% (by weight) respectively. A high lignin content is not very desirable because it adds to the degree of coloration (brown) of the powdered cellulose. In the present invention, there is generally used powdered cellulose having a small particle diameter, with a view to precluding otherwise possible clogging of implements such as, for example, sprayers used for the application of prepared emulsions and ensuring thorough dispersion of droplets of the prepared emulsions being applied by spraying. Generally, 90% of the powdered cellulose to be used herein is desired to have a particle size of up to 177μ (80 Tyler mesh), preferably up to 46μ (300 Tyler mesh). Inclusion of particles with excessively large sizes is not desirable, since they are swelled in water and bring about clogging and other disadvantages from the standpoint of handling. Further the solidified emulsifiable concentrate obtained by using larger particles can not revive a stable emulsion in contact with water.

The powdered cellulose generally exhibits a high absorbing capacity to a liquid; its absorbing capacity is such as to absorb water of a weight two to three times its own weight or an oil of a weight 1.5 to 2.5 times its own weight. By thus using the powdered cellulose, the present invention can obtain a solidified emulsifiable concentrate containing the active ingredient at a high concentration.

Examples of powdered cellulose preparations which are commercially available are shown below.
Soft-texture powdered cellulose:

KC Flock W-300 (trademark of the product by Sanyo Kokusaku Pulp Co., Ltd.)—Water content 4.5%; ash content 0.3%; particle size distribution containing not less than 90% of particles not larger than 46μ; white.

Pump Flock W-1 (trademark of the product by Sanyo Kokusaku Pulp Co., Ltd.)—Water content 5.3%; ash content 1.6%; resin content 2.0%; particle size distribution containing not less than 90% of particles not larger than 177μ; white.

Crystalline cellulose powder:

Avicel (trademark of the product by Asahi Chemical Industry Co., Ltd.)—Water content 5.8%; ash content 0.08%; particle size distribution containing not less than 90% of particles not larger than 125μ; white.
Short-fiber type powdered cellulose:

Water content 7.5%; ash content 5.3%; lignin content 10.5%; particle size distribution containing not less than 90% of particles not larger than 177μ; brown.

An amount to be used of powdered cellulose is in the range of 0.1 to 8.0 times, preferably 0.3 to 2.0 times of the weight of active ingredients. A bulk density of these cellulose is less than 0.5.

In the production of the solidified chemical preparation according to the present invention, there is used an organic solvent to suit the occasion. The organic solvent thus used fulfils its diverse functions of dissolving the active ingredient to give rise to a solution and thereby permitting the active ingredient to be occluded in the powdered cellulose and, at the same time, enabling the active ingredient contained in the produced solidified chemical preparation, upon contact with water, to be dissolved out and uniformly dispersed in the water to give an emulsion. If the active ingredient is of liquid state such that it can easily be occluded in the powdered cellulose without the aid of any other agent and, upon contact with water, can readily produce a stable emulsion through the action of an emulsifier, there is no particular need for using such an organic solvent in the production of the solidified chemical preparation. As the organic solvent, there can be used any of those organic solvents which are adopted in the production of emulsifiable concentrates containing the active ingredient. The organic solvent is desired to be used in the smallest possible quantity in which it accomplishes the purposes mentioned above.

Examples of organic solvents which are advantageously used herein include aliphatic and alicyclic hydrocarbons such as petroleum ether, kerosene, pentane, cyclohexane and solvent naphtha; aromatic hydrocarbons such as benzene, toluene, xylene; chlorinated hydrocarbons such as chloroform, carbon tetrachloride and ethylene chloride; ethers such as ethyl ether and dioxane; ketones such as acetone, methylethyl ketone and cyclohexanone; and dimethylformamide.

The emulsifier fulfils a function of forming a stable emulsion when the solidified emulsifiable concentrate is mixed with water. As the emulsifier mixture according to the invention, there can be used a combination of an anionic surface active agent and a nonionic surface active agent in a particular ratio. Concrete examples of the anionic surface active agents include an alkylaryl sulfonate such as isopropyl naphthalene sulfonate or dodecylbenzene sulfonate. Usually these sulfonates are salts of alkali and alkaline earth metals. It is preferable to use sodium sulfonate or calcium sulfonate.

As the nonionic surface active agent, there can be selected from the group consisting of polyoxyalkylene alkylenearyl ether, polyoxyalkylene alkyl ether, polyoxyalkylene aryl ether, polyoxyalkylene aryl ether polymer, polyoxyalkylene alkyl aryl ether and polyoxyalkylene sorbitan alkylate. The polyoxyalkylene aryl ether is represented by the formula (1)

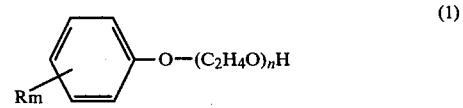

wherein R is phenyl group or styryl group, m is 1 to 3 and n is 10 to 30, preferably 15 to 20.

These examples include polyoxyethylene phenyl ether, polyoxyethylene phenyl phenyl ether and polyoxyethylene distyryl-phenyl ether. The polyoxyalkylene aryl ether polymer means a condensation product of the above compound of the formula (1) and formaldehyde. Said polymer is represented by the formula (2).

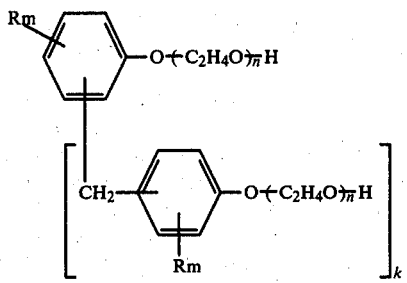

wherein R, m and n are same meanings in the formula (1) and k is 1 or 2.

The mixing ratio of the components of the nonionic and anionic surface active agents is selected to give the best possible emulsifying property.

In general, the anionic surface active agent may be used in an amount of 30 to 60% by weight to the total weight of the emulsifier mixture and it is preferably used in 30 to 50% by weight.

Sometimes, the emulsifiable concentrate may become more or less viscous depending on the kind of emulsifier to be adopted. Such viscosity does not interfere with the desired occlusion of the emulsifiable concentrate in the powdered cellulose.

Although the quantity of the emulsifier to be used is variable with such factors as the kinds and quantities of use of the active ingredient, the organic solvent and the powdered cellulose being used, it is generally on the order of 5 to 30% by weight, preferably 7 to 20% by weight, based on the weights of the active ingredient.

The production of the solidified emulsifiable concentrate by the occlusion in the powdered cellulose of the liquid substance containing the active ingredient can be accomplished simply by adding a suitable quantity of powdered cellulose to the liquid substance and subsequently agitating the resultant mixture. As occasion demands, the production may otherwise be accomplished by adding water to the emulsifiable concentrate to give rise to a concentrated emulsion and causing this emulsion to be occluded in the powdered cellulose as indicated afterward in one preferred embodiment. The product of the occlusion generally does not require any such treatment as drying. There are times when the treatment of drying can bring about undesirable results. When the drying given to the product results in the expulsion of the organic solvent, for example, the active ingredient is eventually educed so that the solidified emulsifiable concentrate, upon dilution with water, will possibly fail to form a stable emulsion.

According to the present invention, various active ingredients of chemical preparations which are sparingly soluble or totally insoluble in water can be converted into solidified emulsifiable concentrates. Examples of active ingredients which are advantageously used in this invention include those enumerated below by way of illustration.

(I) Insecticides
 (a) Organo-phosphorous type—MEP, Malathion, DDVP, Diazino, MPP and Salithion (b) Carbamate type—BPMC, MTMC, MIPC, NAC and XMC
 (c) Pyrethroid type—Allethrin and phthalthrin
 (d) Chlorinated hydrocarbon type—chlorinated benzene
(II) Fungicides—EDDP
(III) Herbicides—Morinate, Simetryne and MCPB.

Of these active ingredients, the present invention is particularly advantageously usable with organo-phosphorus type chemicals and carbamate type chemicals.

In addition to those ingredients mentioned above, the solidified emulsifiable concentrates of the present invention may incorporate therein decomposition inhibitors, efficacy-intensifiers and extenders as generally followed in the production of chemical preparations. Examples of decomposition inhibitors which are usable for the present invention include isopropyl acid phosphate and epichlorohydrin. The used amount of the decomposition inhibitors is 0.05 to 1.0%, preferably 0.1 to 0.5% based on the weight of the produced solid emulsifiable concentrate. Examples of advantageous extenders include inorganic powders such as of sulfates, carbonates, chlorides, phosphates and silicates and organic powders such as of urea, starch, sugar and synthetic resins. It is disadvantageous to use an excess amount of an inorganic extenders such as Kaolin, $SiO_2$ because the solidified emulsifiable concentrate can not generate a stable emulsion in contact with water. These decomposition inhibitors, efficacy-intensifiers, extenders and other additives may be added, depending on their properties, either to liquid substances containing active ingredients and awaiting occlusion in the powdered cellulose or to the powdered cellulose having occluded therein the liquid substances. When necessary, they may be added to the powdered cellulose awaiting occlusion of the liquid substances.

Because of the high absorbing capacity possessed by the powdered cellulose, the solidified emulsifiable concentrate of the present invention can contain the active ingredient in a high concentration. When this solidified emulsifiable concentrate is placed in water, since the absorbing capacity the powdered cellulose exhibits to the active ingredient or its solution in the organic solvent is lowered, the greater part of the active ingredient is immediately released in the form of droplets from the powdered cellulose and, consequently, there is formed a stable emulsified suspension of the powdered cellulose which still retains in an occluded state a small proportion of the active ingredient. Thus, the solidified emulsifiable concentrate of the present invention can be diluted with water to a desired concentration and applied in that state in much the same way as the emulsion prepared from any ordinary emulsifiable concentrate. Owing to the inactiveness of the powdered cellulose, the solidified emulsifiable concentrate of this invention suffers from no appreciable decomposition of the active ingredient while in storage. Since the solidified emulsifiable concentrate of the present invention possesses a moderate wetting property, it avoids shedding dust and consequently provides hygienic handling. Also since it is not required to contain any excess organic solvent, it can be stored and used without entailing any fire hazard or appreciably jeopardizing the environment of hygienic conditions. In the case of the conventional emulsifiable concentrate, its production requires use of a large quantity of organic solvent for the adjustment of concentration. When this emulsifiable concentrate is diluted with water and applied, a relatively large quantity of the organic solvent is scattered in conjunction with the active ingredient inevitably to vitiate the environment. Generally, solvents have varying degrees of toxicity and inflammability and are hazardous from the standpoints of hygiene and fire prevention. Particularly when a large chemical preparation is handled all at once as in the case of aerial application to forests, for example, such solvents can cause various forms of public nuisance including pollution of air, water and soil, emanation of offensive odors and complicated contaminations possibly to involve unexpected hazards. Generally emulsifiable concentrates are stored in vials, cans, drums and other air-tight containers made of glass, galvanized iron, plain iron and synthetic resins. After the contents have been used up, the empty containers require difficult detergence and destruction before they are discarded. These empty containers must be disposed of with full attention paid to preventing them from polluting the environment. For the storage of the solidified emulsifiable concentrates of the present invention, there can be used air-tight containers like bags which are preponderantly made of paper, metallic foils, synthetic resin sheets and other similar sheets. These containers are convenient to handle and economic. After their contents have been used up, the empty containers can easily and safely be disposed of by burning or burying under ground. As described above, the solidified emulsifiable concentrates of the present invention combine the characteristic features of emulsifiable concentrates and those of wettable powders. The advantages which are offered by the solidified emulsifiable concentrates of the present invention may be enumerated as follows:

(1) The production of the solidified emulsifiable concentrate can be accomplished by a very simple procedure of causing the liquid substance containing the active ingredient to be occluded in the powdered cellulose by agitation.

(2) Because of the inactiveness of the powdered cellulose, the active ingredient present in the solidified emulsifiable concentrate does not undergo any conspicuous decomposition, a fact advantageous for the preservation of resources.

(3) Because of the combination of the solidity with the attribute of emulsifiable concentrate, the solidified emulsifiable concentrate of this invention has no inflammability. During its handling or storage, therefore, there is very little possibility of the product entailing any hazard from the standpoint of fire prevention.

(4) Because of the solidity, the product permits use of containers made of paper bags, for example. Such containers are convenient to handle and economic. After their contents have been used up, the empty containers can easily be disposed of.

(5) Since the powdered cellulose has adsorbed the liquid substance substantially to an excess, when the solidified emulsifiable concentrate is diluted with water to form an emulsion suitable for application by spraying, it hardly produces dust. Thus, it can be handled with high safety from the standpoint of health and hygiene.

(6) The solidified emulsifiable concentrate, in spite of its solidity, is converted by dilution with water into an emulsion which is quite stable compared with a suspension of wettable powder.

(7) Since the solidified emulsifiable concentrate contains no or very little organic solvent, it provides great safety from the standpoint of hygiene, compared with the conventional emulsifiable concentrate.

The product of the present invention, as described above, possesses a literally peculiar form and, because of this peculiar form, excels all conventional countertypes in terms of prevention of environmental pollution, fire prevention and preservation of health and hygiene. The product of the present invention has a bulk density more than 0.5.

Now the present invention will be described in full detail herein below with reference to working examples. These working examples are not meant as limitations to the present invention but admit of modifications thereto without departing from the spirit of the invention. The numerical values of "change by aging," "ratio of emulsification," and "ratio of suspension" which are given in the following working examples were determined as indicated below:

Change by aging:

To be determined by allowing a given preparation to stand in a closed containers (bag of aluminum foil) at 40° C. for 30 days, finding at the end of the standing the proportion of the active ingredient undergone decomposition during the standing and calculating the percentage of this proportion to the whole of the active ingredient present at the beginning of the standing.

Ratio of emulsification:

To be determined by placing 2.5 g of a given preparation in a 250-ml measuring cylinder, diluting it with added water to a total volume of 250 ml, allowing the diluted preparation to stand at rest for 15 minutes, then repetitively turning the cylinder upside down 30 times for a minute to cause dispersion and emulsification of the contents, again allowing the contents to stand at rest for 15 minutes, subsequently suction filtering 30 ml of the upper-layer liquid with a filter paper No. 6 (chemical analysis grade), assaying a 10-ml portion of the filtrate to find the quantity of components contained therein and calculating the percentage of the found quantity of components to the quantity of components contained originally in 0.1 g of the preparation.

Ratio of suspension:

To be determined by placing 2.5 g of a given preparation in a 250-ml measuring cylinder, diluting it with added water to a total volume of 250 ml, allowing the diluted preparation to stand at rest for 15 minutes, then repetitively turning the cylinder upside down 30 times for a minute to cause dispersion and emulsification of the contents, again allowing the contents to stand at rest for 24 hours, extracting at the end of a standing a 10-ml sample through the central portion of the measuring cylinder, assaying the sample to find the quantity of components contained therein and calculating the percentage of the found quantity of components to the quantity of components contained originally in 0.1 g of the preparation.

The symbols which are used in the following working examples have the following meanings:

PAP: Decomposition inhibitor (isopropyl acid phosphate)

EC: Decomposition inhibitor (epichlorohydrin)

E: Emulsifier (to be specifically designated by numerations as shown below)

No. 1—Composition as follows (by weight ) . . . present invention

Polyoxyethylene (EO 20 mol) distyryl phenyl ether—27%

Polyoxyethylene (EO 18 mol) distyryl phenyl ether polymer—35%
Calcium dodecyl benzene sulfonate—38%
No. 2—Compositon (by weight) . . . present invention
Polyoxyethylene (EO 20 mol) diphenylphenyl ether—35%
Polyoxyethylene (EO 18 mol) distyrylphenyl ether—32%
Sodium dodecylbenzene sulfonate—33%
No. 3—Composition (by weight) . . . control
Polyoxyethylene (EO 20 mol) nonylphenyl ether—30%
Polyoxyethylene (EO 18.5 mol) oleyl ether—30%
Calcium dodecylbenzene sulfonate—40%
No. 4—Composition (by weight) . . . control
Polyoxyethylene (EO 10 mol) distyrylphenyl ether—50%
Calcium dodecylbenzene sulfonate—50%
No. 5—Compositon (by weight) . . . control
Polyoxyethylene (EO 20 mol) sorbitan monostearate—60%
Calcium dodecylbenzene sulfonate—40%
CP: Powdered cellulose (to be specifically designated by numerations as shown below)
No. 1—Soft-textured powdered cellulose (sold under trademark "KC Flock W-300" by Sanyo Kokusaku Pulp Co., Ltd.: water content 4.5%, ash content 0.3%, particle size distribution containing not less than 90% of particles not larger than 46μ, white)
No. 2—Crystalline cellulose powder (sold under trademark "Avicel" by Asahi Chemical Industry Co., Ltd.: water content 5.8%, ash content 0.08%, particle size distribution containing not less than 90% of particles not larger than 125μ, white)
No. 3—Soft-textured powdered cellulose (sold under trademark "Pulp Flock W-1" by Sanyo Kokusaku Pulp Co., Ltd.: water content 5.3%, ash content 1.6%, resin content 2.0%, particle size distribution containing not less than 90% of particles not larger than 177μ, white)
No. 4—Short-fiber powdered cellulose (water content 7.5%, ash content 5.3%, lignin content 10.5%, particle size distribution containing not less than 90% of particles not larger than 177μ, brown)

The agricultural pesticides or sanitary chemicals of the formulations which are indicated in the following working examples were prepared, unless specifically indicated otherwise, by first converting given technical-grade active ingredients into respective solutions by addition thereto of emulsifiers, when necessary, in conjunction with decomposition inhibitors and solvents, then adding powdered cellulose (abbreviated as CP hereinafter), when necessary, in conjunction with extenders to the solutions and agitating the resultant mixtures by use of a portable kneader and thereby causing the liquid components to be occluded in the CP. Wherever percentages are mentioned hereinafter, they are percentages by weight unless specifically indicated otherwise. (The controls which were conventional emulsifiable concentrates are indicated in the tables to show differences in the quantities of relevant chemicals used.)

EXAMPLE 1

Water-insoluble liquid insecticide, MEP (dimethyl-3-methyl-4-nitrophenyl phosphorothionate)

|  | 1 | 2 | 3 | Control 1 | Control 2 |
|---|---|---|---|---|---|
| MEP | 54 | 54 | 11 | 54 | 54 |
| PAP | 0.3 | 0.3 | 0.1 | 0.3 | 0.3 |
| MAL | — | — | 5 | — | — |
| E (No. 1) | 6 | 6 | 0.9 | 6 | 15 |
| C. P. | (No. 1) 36.7 | (No. 1) 39.7 | (No. 3) 5 | — | — |
| SiO$_2$ | 3 | — | — | 39.7 | — |
| Kaolin | — | — | 78 | — | — |
| Xylene | | | | | 31 |
| Change by aging | 1.1 | 0.5 | 2.2 | 2.1 | 2.7 |
| Ratio of emulsification | 98.6 | 92.6 | 75.6 | 0 | |
| Ratio of suspension | 96.5 | 98.3 | 98.5 | 0 | |

In the table, Formulation 3 is a sanitary chemicals preparation, Control 1 and Control 2 are conventional preparations in the form of wettable powder and emulsifiable concentrate respectively, MAL stands for lauryl methacrylate as a deodorant and SiO$_2$ for white carbon having an average particle diameter of not more than 5μ.

EXAMPLE 2

Water-insoluble liquid fungicide, EDDP (O-ethyl-diphenyl phosphorodithiolate)

|  | 1 | 2 | 3 | Control |
|---|---|---|---|---|
| EDDP | 58 | 58 | 58 | 32 |
| PAP | 0.3 | 0.3 | 0.3 | |
| E (No. 1) | 4 | 4 | 4 | 20 |
| C. P. | (No. 2) 37.7 | (No. 3) 30 | (No. 3) 30 | |
| Kaolin | — | 7.7 | — | |
| Na$_2$SO$_4$ | — | — | 7.7 | |
| Xylene | | | | 48 |
| Change by aging | 2.8 | 3.1 | 2.9 | 3.6 |
| Ratio of emulsification | 92.5 | 90.3 | 91.8 | |

In the table, Control is a conventional emulsifiable concentrate. (This invariably applies hereinafter.)

EXAMPLE 3

Water-insoluble solid insecticide, BPMC (2-secondary-butyl-phenyl N-methylcarbamate) having a melting point of 30° C.

|  | 1 | 2 | Control |
|---|---|---|---|
| BPMC | 51 | 22 | 51 |
| Dodecylbenzene (Solvent) | 5 | 2 | |
| E (No. 1) | 8 | 3 | 10 |
| PAP | 0.5 | 0.2 | |
| C. P. | (No. 1) 35.5 | (No. 3) 20 | |
| Grape sugar | — | 52.8 | |
| Xylene | | | 39 |
| Change by aging | 1.5 | 2.1 | 4.6 |
| Ratio of emulsification | 95.3 | 93.6 | |

EXAMPLE 4

Water-insoluble liquid insecticide, Diazinon (diethyl-2-isopropyl-4-methyl-6-pyrimidinyl phosphorothionate)

|  | 1 | 2 | 3* | Control |
|---|---|---|---|---|
| Diazinon | 51 | 5.5 | 5.5 | 35 |
| E. C. | 0.3 | 0.1 | 0.1 |  |
| E (No. 1) | 6 | 1 | 1 | 20 |
| C. P. | (No. 1) | (No. 3) | (No. 1) |  |
|  | 42.7 | 4 | 40 |  |
| NaHCO₃ | — | 89.4 | — |  |
| Water | — | — | 53.4 |  |
| Xylene |  |  |  | 45 |
| Change by aging | 2.3 | 1.5 | 1.8 | 2.6 |
| Ratio of emulsification | 96.3 | 95.4 | 96.5 |  |

*This preparation was produced by agitating Diazinon with EC and E to form a uniform solution, then agitating this solution with added water to form an emulsion, and finally agitating the emulsion with added CP and thereby causing CP to occlude the liquid substance therein.

EXAMPLE 5

Water-insoluble liquid insecticide, Malathion (S-[1,2-bis (ethoxycarbonyl)ethyl] dimethyl phosphorothiolothionate)

|  | 1 | 2 | 3 | 4 | Control |
|---|---|---|---|---|---|
| Malathion | 54 | 54 | 23 | 65 | 52 |
| PAP | 0.3 | 0.3 | 0.2 | 0.2 |  |
| E (No. 1) | 6 | 6 | 3 | 4.8 | 20 |
| C. P. | (No. 1) | (No. 1) | (No. 3) | (No. 1) |  |
|  | 39.7 | 30 | 15 | 30 |  |
| Polyvinyl alcohol | — | 1 | 1 | — |  |
| Kaolin | — | 8.7 | 57.8 | — |  |
| Xylene |  |  |  |  | 28 |
| Change by aging | 2.1 | 2.8 | 3.1 | 2.0 | 3.0 |
| Ratio of emulsification | 95.3 | 94.1 | 86.6 | 90.3 |  |

EXAMPLE 6

Water-insoluble liquid insecticide, DDVP (2,2-dichlorovinyl dimethyl phosphate)

|  | 1 | 2 | Control |
|---|---|---|---|
| DDVP | 52 | 67 | 52 |
| PAP | 0.5 | 0.5 |  |
| E (No. 1) | 5 | 5.5 | 20 |
| C. P. (No. 1) | 42.5 | 27 |  |
| Xylene |  |  | 28 |
| Change by aging | 3.4 | 2.8 | 3.5 |
| Ratio of emulsification | 98.3 | 99.5 |  |

EXAMPLE 7

Water-insoluble liquid herbicide, Morinate (S-ethylhexahydro-1H-azepin-1-carbothioate); water-insoluble solid herbicide, Simetryne [2-methylthio-4,6-bis(ethylamino)-S-triazin]; and water-insoluble liquid herbicide, MCPB (ethyl 2-methyl-4-chlorophenoxy butyrate)

|  | 1 | 2 | Control |
|---|---|---|---|
| Morinate | 45 | 8.5 | No preparation of the form of emulsifiable concentrate available to date. |
| Simetryne | 8.5 | 1.5 |  |
| MCPB | 4.5 | 0.8 |  |
| E (No. 1) | 6 | 1.5 |  |
| C. P. (No. 4) | 36 | 7 |  |
| Pumice (1.5-0.5 mm. dia.) | — | 80.7 |  |
| Change by aging (Morinate) | 1.8 | 1.3 |  |
| Ratio of emulsification (Morinate) | 97.5 | 96.3 |  |

EXAMPLE 8

Water-insoluble liquid fungicide, EDDP (O-ethyl-diphenyl phosphorodithiolate) and water-insoluble liquid insecticide, MPP (dimethyl-4-methylthio-m-tolyl phosphorothionate)

|  |  | 1 | 2 | 3 | Control 1 | Control 2 |
|---|---|---|---|---|---|---|
| EDDP |  | 23 | 2.8 | 2.8 | 2.8 | 23 |
| MPP |  | 32 | 2.3 | 2.3 | 2.3 | 32 |
| PAP |  | 0.5 | 0.3 | 0.3 | 0.3 |  |
| E (No. 1) |  | 6 | 0.8 | 0.8 | 0.8 | 20 |
| C. P. |  | (No. 1) | (No. 3) | (No. 4) |  |  |
|  |  | 38.5 | 4 | 4 | — |  |
| SiO₂ |  | — | — | 1 | 3 |  |
| Kaolin |  | — | 89.8 | 88.8 | 90.8 |  |
| Xylene |  |  |  |  |  | 27 |
| Change by aging | (EDDP) | 2.5 | 2.6 | 3.4 | 2.3 | 3.0 |
|  | (MPP) | 1.8 | 2.1 | 2.5 | 1.5 | 2.5 |
| Ratio of emulsification | (EDDP) | 91.3 | 71.3 | 51.3 | 0 |  |
|  | (MPP) | 92.5 | 71.8 | 52.5 | 0 |  |

In the table, Control 1 is a conventional dust preparation and Control 2 is a conventional emulsifiable concentrate preparation.

EXAMPLE 9

Water-insoluble solid insecticide, Salithion (2-methoxy-4H-1,3,2-benzodioxaphosphorin-2-sulfide)

The solidification was effected by dissolving Salithion in solvents Anon or Isophoron under heating, mixing the resultant solution uniformly with E and PAP and thereafter agitating the resultant mixture with CP and thereby causing CP to occlude the liquid substance.

|  | 1 | 2 | Control |
|---|---|---|---|
| Salithion | 28 | 28 | 28 |
| Anon | 27.5 | 25 | 15 |
| Isophoron | — | 2.5 |  |
| E (No. 1) | 6 | 6 | 12 |
| PAP | 0.5 | 0.5 | 0.5 |
| C. P. | 38 | 38 |  |
| Xylene |  |  | 44.5 |
| Change by aging | 4.0 | 3.8 | 4.2 |
| Ratio of emulsification | 79.3 | 82.6 |  |

EXAMPLE 10

Water-insoluble liquid insecticide (orthodichlorobenzene) and water-insoluble liquid fungicide (meta-cresol)

The solidification was effected by mixing orthodichlorobenzene, meta-cresol, E, perfume and dyestuff to form a uniform solution and agitating this solution with CP and thereby causing the CP to occlude the liquid substance therein.

|  | 1 | 2 | Control |
|---|---|---|---|
| Orthodichlorobenzene | 51 | 51 | 50 |

-continued

|  | 1 | 2 | Control |
|---|---|---|---|
| Meta-cresol | 7 | 7 | 7 |
| E (No. 1) | 10 | 10 | 15 |
| Perfume | — | 0.5 | |
| Dyestuff | — | 0.5 | |
| C. P. (No. 1) | 32 | 31 | |
| Kerosene | | | 14 |
| Xylene | | | 14 |
| Ratio of emulsification (orthodichlorobenzene) | 91.6 | 92.3 | |

Note
Perfume: Synthetic pine needle type perfume.
Dyestuff: Brilliant blue FCF

EXAMPLE 11

Water-insoluble liquid insecticide (allethrin), water-insoluble solid insecticide (phthalthrin) and water-insoluble liquid insecticide, MEP (dimethyl-3-methyl-4-nitrophenyl phosphorothionate).

|  | 1 | 2 | 3 | Control 1 | 2 | 3 |
|---|---|---|---|---|---|---|
| Allethrin | 5 | — | 2 | | 2 | |
| Phthalthrin | — | 5 | — | 5 | | 2 |
| MEP | — | — | 10 | | 5 | |
| Cinetrin | 5 | 10 | — | 5 | 10 | 10 |
| PAP | 0.5 | 0.5 | 0.5 | — | — | |
| E (No. 1) | 1.5 | 1.5 | 2 | 10 | 15 | 10 |
| C. P. (No. 1) | 8 | 10 | 10 | | | |
| Na$_2$SO$_4$ | 27 | — | 55 | | | |
| Starch | 26 | 36 | — | | | |
| Lactose | 27 | 37 | 20.5 | | | |
| Xylene | | | | 80 | 68 | 78 |
| Change by aging | 1.2 | 1.0 | 0.9 | 2.0 | 2.1 | 1.5 |
| Ratio of emulsification | 95.8 | 98.6 | 94.3 | | | |

Cinetrin (ethylhexyl bicycloheptane dicarboxyimide) is an efficacy enhancer.

EXAMPLE 12

For referential purpose, the effect of the mixing ratio of powdered cellulose and white carbon (SiO$_2$) according to the method of this invention upon the ratio of emulsification was studied. It was consequently ascertained that where the powdered cellulose content was 36%, the ratio of emulsification could be retained within the range of practicability insofar as the SiO$_2$ content did not exceed 4%. The result are graphically shown in the accompanying drawing.
Referential Example:
Effect of mixing ratio of C. P. and SiO$_2$ upon the ratio of emulsification.

|  | 1 | 2 | 3 | 4 | 5 | 6 | 7 | 8 | 9 | 10 | 11 |
|---|---|---|---|---|---|---|---|---|---|---|---|
| Malathion | 54 | 54 | 54 | 54 | 54 | 54 | 54 | 54 | 54 | 54 | 54 |
| PAP | 0.3 | 0.3 | 0.3 | 0.3 | 0.3 | 0.3 | 0.3 | 0.3 | 0.3 | 0.3 | 0.3 |
| E (No. 1) | 6 | 6 | 6 | 6 | 6 | 6 | 6 | 6 | 6 | 6 | 6 |
| C. P. (No. 1) | 39.7 | 35.7 | 31.7 | 27.7 | 23.7 | 19.7 | 15.7 | 11.7 | 7.7 | 3.7 | — |
| SiO$_2$ | — | 4 | 8 | 12 | 16 | 20 | 24 | 28 | 32 | 36 | 39.7 |
| Ratio of emulsification | 95.3 | 84.7 | 54.3 | 36.0 | 16.1 | 8.3 | 2.7 | 1.1 | 0.3 | 0 | 0 |

EXAMPLE 13

For referential purpose, the effect of the mixing ratio of an anionic surface active agent and a nonionic surface active agent according to the present invention was studied.

Emulsion concentrates containing various active ingredients and Emulsifier No. 1 to No. 5 were prepared according to the composition listed in the following table.

|  | Active ingredient | Amount | Solvent (Amount) | Emulsifier Amount |
|---|---|---|---|---|
| 1 | MEP | 50 | — | 7 |
| 2 | EDDP | 50 | — | 7 |
| 3 | Diazinon | 50 | — | 7 |
| 4 | Malathion | 50 | — | 7 |
| 5 | BPMC | 50 | Dodecylbenzene (5) | 7 |
| 6 | Ortho-dichlorobenzene | 50 | m-cresol (7) | 7 |

(A unit is weight part)

To the each emulsion concentrate was added water so as to be the concentration of 1% by weight. Aqueous emulsion thus obtained stood for 2 hours at the room temperature and judged by eye. The results were shown in the table.

| | Active ingredient | | | | | |
|---|---|---|---|---|---|---|
| Emulsifier | MEP | EDDP | Diazinon | Malathion | BPMC | o-dichlorobenzene |
| E No. 1 | — | — | — | — | — | — |
| E No. 2 | — | — | — | — | — | — |
| E No. 3 | + | + | — | + | + | + |
| E No. 4 | + | + | — | + | + | + |
| E No. 5 | + | + | + | + | + | + |

Note
— means stable emulsion.
+ means separation into two layers.

EXAMPLE 14

Effect of the particle size of powdered cellulose preparation

Various emulsion concentrates were prepared by using Emulsifiers of No. 1 according to the Example 13 of the present specfication. To each emulsion concentrate was added C. P. (No. 4) to give 100 parts of total weight, which was the present emulsifiable concentrate. On the other hand, 100 parts of the emulsifiable concentrate was mixed with 25 parts of water and granulated by the extruder and dried at 50°–60° C. for 12 hours to give particles having a particle diameter of 1 mm (16 Tyler mesh). According to a similar manner, granules of a particle size of 2.38 mm (8 Tyler mesh) was produced.
Test method (Ratio of emulsification:)
To be determined by placing 2.5 g of the samples in a 250 ml measuring cylinder, diluting it with added water to a total volume of 250 ml, allowing to stand for 15 minutes, then repetitively turning the cylinder upside down 30 times for a minute to cause dispersion, again allowing the contents to stand for 15 minutes. 30 ml of upper layer solution was taken out and filtered by No. 6 filter paper (chemical analysis grade), assaying the 10 ml portion of the filtrate to find the quantity of components contained therein and calculating the percentage of the found quantity of components to the quantity of components contained originally in 0.1 g of the preparation.

Results

| Active Ingredients | Sample Present Invention | Granules φ1 mm | Granules φ2.38 mm |
|---|---|---|---|
| MEP | 93.8 (%) | 16.1 (%) | 15.2 (%) |
| EDDP | 92.9 | 18.7 | 16.5 |
| Diazinon | 95.3 | 49.1 | 33.5 |
| Malathion | 96.2 | 35.7 | 29.6 |
| BPMC | 94.1 | 31.3 | 28.8 |
| o-dichloro-benzene | 90.5 | — | — |

I claim:

1. A solidified emulsifiable concentrate for agricultural or sanitary use, which comprises: powdered cellulose having the ability to absorb 2 to 3 times its weight in water, 90% of said powdered cellulose having a particle size of up to 177μ and a liquid mixture which is occluded in the powdered cellulose, said liquid mixing being formed by mixing an agriculturally or sanitary active ingredient sparingly soluble or totally insoluble in water or aqueous solution, in an organic solvent which has the capability of dissolving said active ingredient so that said active ingredient can be absorbed by said cellulose with an emulsifier mixture comprising alkylbenzene sulfonate and at least one nonionic surfactant selected from the group consisting of polyoxyalkylene alkylenearyl ether, polyoxyalkylene alkyl ether, polyoxyalkylene aryl ether, polyoxyalkylene alkylaryl ether, polyoxyalkylene aryl ether polymer and polyoxyalkylene sorbitan alkylate, the amount of said alkylbenzene sulfonate being 30 to 60% by weight in said emulsifier mixture, in an effective quantity sufficient to enable said active ingredient or aqueous solution thereof to be stably emulsified in water when said concentrate is mixed with water with the proviso that if said active ingredient is liquid, the organic solvent may be excluded.

2. The concentrate of claim 1, wherein said liquid mixture is prepared by mixing an active liquid ingredient with the emulsifier mixture at room temperature.

3. The concentrate of claim 1, wherein said liquid mixture is prepared by mixing an active solid ingredient with the emulsifier mixture in an organic solvent at room temperature.

4. The concentrate of claim 1, wherein the emulsifier mixture comprises alkylbenzene sulfonate and a nonionic surfactant of polyoxyalkylene aryl ether and/or polyoxyalkylene aryl ether polymer.

5. The concentration of claim 1, wherein the amount of said alkylbenzene sulfonate is 30 to 50% by weight in said emulsifier mixture.

6. The concentration of claim 4, wherein the polyoxyalkylene aryl ether is represented by the formula;

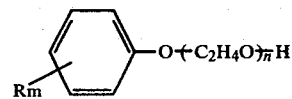

wherein R is styryl group or phenyl group, m is 1 to 3 and n is 15 to 20.

7. The concentrate of claim 4, wherein the polyoxyalkylene aryl ether polymer is a condensation product of formaldehyde and the polyoxyalkylene aryl ether having the formula (1)

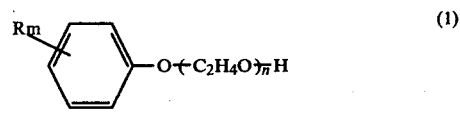

(1)

wherein R is styryl group or phenyl group, m is 1 to 3 and n is 15 to 20, the said polymer having the formula (2)

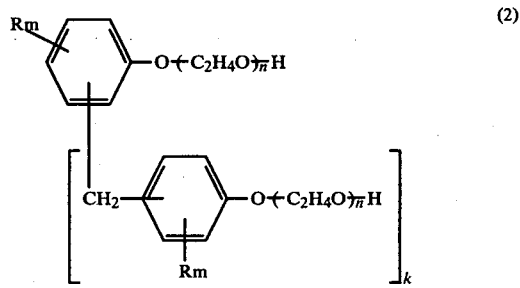

(2)

wherein R, m and n are same meanings in the formula (1) and k is 1 or 2.

8. The concentrate of claim 4, wherein the alkylbenzene sulfonate is alkali and an alkaline earth metal salt of dodecylbenzene sulfonic acid.

9. The concentrate of claim 8, wherein the alkylbenzene sulfonate is sodium alkylbenzene sulfonate or calcium alkylbenzene sulfonate.

10. The concentrate of claim 1, further comprising an agent which inhibits the decomposition of said active ingredient.

11. The concentrate of claim 1, wherein at least 90% of all of the particles of said powdered cellulose have a particle diameter of up to 46μ.

12. The concentrate of claim 1, wherein the powdered cellulose has a bulk density of up to 0.5.

13. The concentrate of claim 1, said active ingredient is an organophosphoric acid ester.

14. The concentrate of claim 1, wherein said active ingredient is a carbamic acid.

15. The concentrate of claim 1, wherein said active ingredient is a pyrethroid.

16. The concentrate of claim 1, wherein said concentrate has a bulk density more than 0.5.

17. The concentrate of claim 1, wherein said active ingredient is chlorinated benzene.

18. A method for the application of the solidified emulsifiable concentrate of claim 1, which comprises mixing said emulsifiable concentrate with an effective amount of water thereby producing a stable emulsion; and applying said stable emulsion to the desired agricultural object or object to be sanitized for treatment.

* * * * *